(12) United States Patent
Morrissette et al.

(10) Patent No.: US 9,173,697 B2
(45) Date of Patent: Nov. 3, 2015

(54) SURGICAL CANNULA FOR DISSIPATING ELECTRIC CHARGE

(75) Inventors: Tyler J. Morrissette, Niantic, CT (US); Joseph P. Orban, III, Norwalk, CT (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 985 days.

(21) Appl. No.: 12/946,693

(22) Filed: Nov. 15, 2010

(65) Prior Publication Data
US 2012/0078245 A1    Mar. 29, 2012

Related U.S. Application Data

(60) Provisional application No. 61/387,843, filed on Sep. 29, 2010.

(51) Int. Cl.
*A61B 18/14* (2006.01)
*A61B 19/00* (2006.01)

(52) U.S. Cl.
CPC ............... *A61B 18/14* (2013.01); *A61B 19/201* (2013.01); *A61B 19/2203* (2013.01); *A61B 2018/1425* (2013.01)

(58) Field of Classification Search
USPC .................... 606/27, 34, 41, 167; 604/158
See application file for complete search history.

(56) References Cited

U.S. PATENT DOCUMENTS

| | | | | |
|---|---|---|---|---|
| 3,659,610 A * | 5/1972 | Cimber | ........................ | 604/157 |
| 4,692,140 A * | 9/1987 | Olson | ............................ | 604/40 |
| 5,052,927 A * | 10/1991 | Discko, Jr. | ..................... | 433/90 |
| 5,312,401 A * | 5/1994 | Newton et al. | .................. | 606/46 |
| 5,387,196 A | 2/1995 | Green et al. | | |
| 5,431,638 A * | 7/1995 | Hennig et al. | ................ | 604/264 |
| 5,515,478 A * | 5/1996 | Wang | ............................ | 700/251 |
| 5,520,685 A * | 5/1996 | Wojciechowicz | .............. | 606/49 |
| 5,630,813 A * | 5/1997 | Kieturakis | ....................... | 606/46 |
| 5,792,141 A * | 8/1998 | Logeman | ......................... | 606/46 |
| 5,855,563 A * | 1/1999 | Kaplan et al. | ................ | 604/509 |
| 5,868,742 A * | 2/1999 | Manes et al. | .................... | 606/46 |
| 6,132,368 A * | 10/2000 | Cooper | ........................ | 600/102 |
| 6,679,886 B2 * | 1/2004 | Weikel et al. | ..................... | 606/79 |
| 6,840,938 B1 * | 1/2005 | Morley et al. | .................... | 606/51 |
| 8,375,808 B2 | 2/2013 | Blumenkranz et al. | | |
| 2004/0267203 A1 * | 12/2004 | Potter et al. | ............. | 604/164.05 |
| 2005/0256368 A1 * | 11/2005 | Klenk et al. | .................... | 600/37 |
| 2007/0191734 A1 * | 8/2007 | Grigoryants et al. | ......... | 600/564 |
| 2007/0203517 A1 * | 8/2007 | Williams et al. | ............. | 606/191 |
| 2008/0009697 A1 * | 1/2008 | Haider et al. | ................ | 600/407 |
| 2008/0161677 A1 * | 7/2008 | Sutherland et al. | ........... | 600/417 |
| 2010/0042097 A1 | 2/2010 | Newton et al. | | |

* cited by examiner

*Primary Examiner* — Michael Peffley
*Assistant Examiner* — Daniel Flower

(57) ABSTRACT

A cannula subject to receiving electric charge via capacitive coupling is configured to provide an easily connectable path to remove the charge. The cannula is further configured with a flared distal end to prevent scraping contact with a surgical instrument shaft. Embodiments of the cannula may be used in surgical procedures in which the cannula does not contact the patient.

23 Claims, 3 Drawing Sheets

SURGICAL CANNULA FOR DISSIPATING ELECTRIC CHARGE

CROSS-REFERENCE TO RELATED APPLICATIONS

This application claims the benefit under 35 U.S.C. §119(e) of U.S. Patent Application No. 61/387,843 (filed Sep. 29, 2010; entitled "Grounded Cannula"), which is incorporated herein by reference.

BACKGROUND

1. Field of Invention

The present invention relates generally to surgical instruments, and more specifically to an apparatus for dissipating electric charge on surgical instruments.

2. Art

The use of robotic surgery, for example the use of da Vinci® telerobotic surgical systems, commercialized by Intuitive Surgical, Inc., Sunnyvale, Calif., is increasing. Robotic surgery allows complex surgical procedures to be executed with minimally invasive techniques. A smaller incision heals faster, is less painful, is less prone to infections, and leaves less noticeable scarring. Teleoperated surgical instruments under endoscopic view often allow a surgeon to carry out actions that are difficult to do with manual instruments. For these and other reasons, patients, surgeons, and hospital personnel are becoming inclined towards robotic surgery over traditional manual procedures (open or minimally invasive).

Robotic surgery instruments include items such as cannulas, graspers, forceps, scissors, retractors, stabilizers, and other instruments that may or may not be made of metal or other electrically conductive materials. Conductive materials may pose a hazard in a surgical environment because they may become electrically charged. When these materials suddenly discharge, the discharge may cause burns or other injuries to the patient, the surgeon, or other personnel as the charge seeks a path to a lower electric potential. Since the discharge arc may be out of the surgeon's field of view, the surgeon may not realize that a patient burn has occurred. And, since the instruments are long, even if a discharge is sensed, it may be difficult to identify the burn location. In addition, such a sudden discharge may damage the instrument itself if the instrument includes electrical components.

Typically, the energy stored in a surgical instrument from capacitive coupling during robotic surgery is transferred to the patient in two ways. First, the stored charge can be drained by keeping the instrument in direct, physical contact with the patient's body. This constant contact conducts electric charge from the instrument to the patient's tissues, which prevents arcing by establishing an equal electric potential on the patient and the instrument. For example, charge that is induced on an instrument cannula that is placed through the patient's body wall will drain to the patient because of the cannula's direct contact with the patient. Second, the stored electric charge may be drained via capacitive coupling to a second instrument that is in direct, physical contact with the patient. As described above, the contact between the second instrument and the patient then conducts the transferred charge to the patient. For example, unwanted charge may build up on certain portions of a monopolar electrocautery instrument, such as on a metal flexible wrist mechanism that supports the energized end effector. Without a conductive path or effective insulation, this charge may arc from the instrument to the patient and cause injury. But this unwanted charge can be safely transferred via capacitive coupling to the cannula though which the electrocautery instrument extends. The transferred charge is then conducted from the cannula to the patient via direct contact.

To conduct the unwanted charge away from the patient, one or more patient return electrodes, such as those associated with an electrocautery instrument, are placed in contact with the patient. The patient return electrode completes a circuit that safely removes the electric charge from the patient, so that arcing does not occur at some other location on the body.

In certain new robotic surgery procedures, however, an instrument that is subject to capacitive coupling will not come into direct contact with the patient's tissues. Therefore, electric charge buildup on the instrument from capacitive coupling occurs because there is no path to drain the built up charge. In transoral robotic surgery (TORS), for example, an instrument cannula is inserted into oral cavity in order to guide and support a telerobotically controlled surgical instrument, but often the cannula does not contact the patient. Therefore, when an electrosurgical instrument (e.g., a monopolar electrocautery instrument) is inserted through a cannula during a TORS procedure, capacitive coupling between the instrument and its cannula may cause electric charge buildup on the cannula. Since the instrument cannula with the charge buildup is often in close proximity to, although not in contact with, the patient's tissues, sufficiently high charge buildup may cause a dangerous electrical arc between the instrument cannula and the patient. Likewise, a person who inadvertently comes near or touches the charged instrument cannula may be similarly injured, or electrical components that come near or touch the charged instrument cannula may be damaged. Similarly, since there is no suitable conductive path from the cannula, unwanted charge that builds up on a portion of the instrument that extends through the cannula (e.g., on one or more electrocautery instrument components) cannot be drained via capacitive coupling to the cannula, because once charged the cannula itself does not offer a relatively lower electric potential.

Since electrical charge buildup is not being continuously dissipated through the patient's body, the charge will remain concentrated on one or more instruments. This concentrated charge buildup creates a hazardous condition, as described above. Consequently, there is a need in the art to dissipate energy from instruments, and specifically an instrument cannula, that do not contact the patient.

The cantilever aspect of a supporting cannula that does not contact the patient presents another potential problem. When an instrument extends through a cannula, heavy side loading on the instrument's distal end pushes the instrument laterally against the cannula's distal end. During withdrawal (e.g., during a surgical procedure as the instrument experiences numerous small insertion and withdrawal motions as the slave instrument responds to the surgeon's teleoperation master inputs), the distal end of a cannula may scrape against the instrument shaft. This scraping may, in some instances, remove a small piece of the shaft, which may then enter a patient.

In order to assure that a cannula can be inserted through a patient's body wall, the distance between the cannula's inner diameter at its distal end and the outer diameter of the cannula obturator used to pierce the body wall needs to be minimized. Otherwise, cannula insertion through the body wall is difficult. But when the obturator is removed and replaced with an instrument, the cannula's distal end configuration that is needed for proper insertion through the body wall may lead to instrument shaft scraping under high instrument side loads.

Therefore, there is a need to prevent scraping contact between a cannula's distal end and the instrument shaft.

SUMMARY

In order to reduce an electric charge from capacitive coupling on a cannula, the cannula is configured with a plug section that allows a patient return electrode to be electrically connected to the cannula. The return electrode is then placed in contact with the patient. The patient is similarly coupled to a reference electrical potential that is associated with an electrosurgical energy generator unit that supplies energy to a surgical instrument that is inserted through the cannula. In addition, although apparently not practical for a cannula that is normally inserted through a patient's body wall, in an aspect of the invention the distal end of cannula is flared outwards to prevent scraping contact between the cannula's distal end and the instrument shaft.

DETAILED DESCRIPTION

Figure 1A:
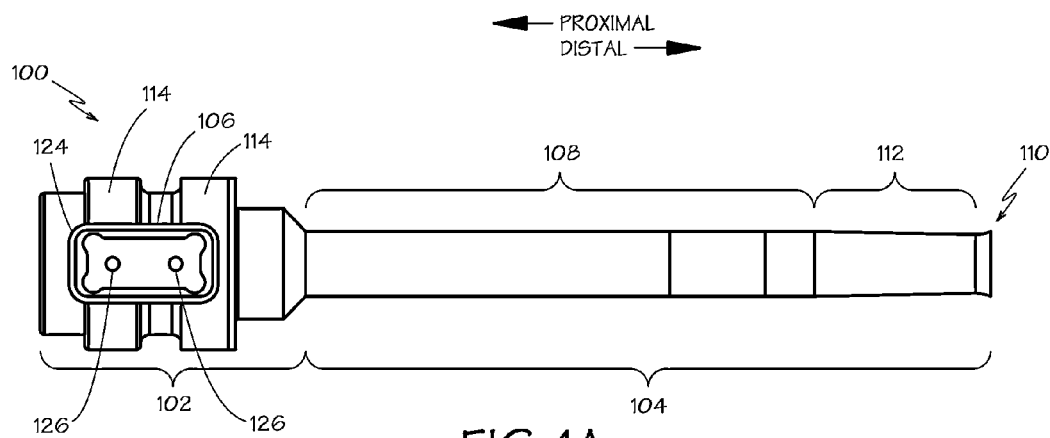
FIG. 1A is a top view of a cannula.

This description and the accompanying drawings that illustrate inventive aspects and embodiments should not be taken as limiting—the claims define the protected invention. Various mechanical, compositional, structural, electrical, and operational changes may be made without departing from the spirit and scope of this description and the claims. In some instances, well-known circuits, structures, and techniques have not been shown or described in detail in order not to obscure the invention. Like numbers in two or more figures represent the same or similar elements. Diagrammatic figures are intended to be illustrative and are not to scale.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes includes various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components. Mathematical and geometric terms are not necessarily intended to be used in accordance with their strict definitions unless the context of the description indicates otherwise, because a person having ordinary skill in the art would understand that, for example, a substantially similar element that functions in a substantially similar way could easily fall within the scope of a descriptive term even though the term also has a strict definition.

Elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

Figure 1B:
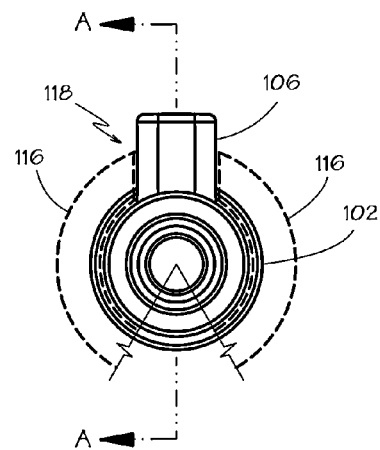
FIG. 1B is a proximal end view of the cannula shown in FIG. 1A.
Figure 1C:
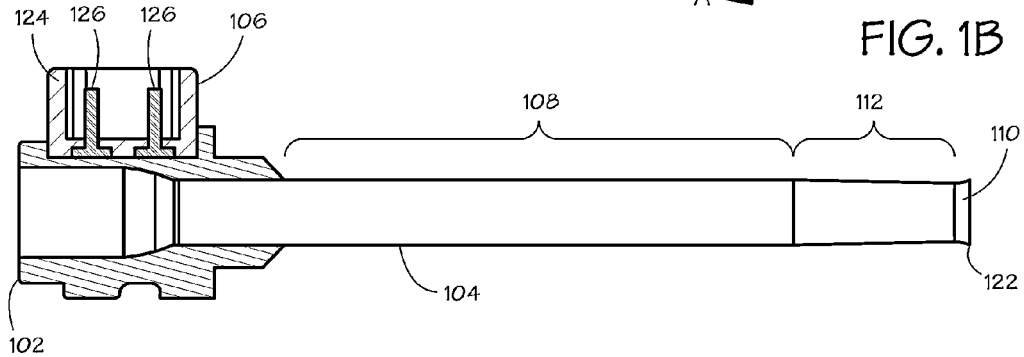
FIG. 1C is a side elevation cross-sectional view of the cannula shown in FIG. 1A.

FIG. 1A is a top view of a cannula 100 that embodies aspects of the invention. FIG. 1B is a proximal end view of the embodiment shown in FIG. 1A, and FIG. 1C is a side elevation cross-sectional view taken at cut line A-A in FIG. 1B. Proximal and distal orientations are as indicated by the arrows in FIG. 1A. Cannula 100 includes three main features: a mounting section 102, a tube section 104, and a plug section 106. As shown in FIG. 1, the proximal end of tube section 104 is joined to the distal end of mounting section 102, and plug section 106 is joined to the side of mounting section 102. Tube section 104 is further divided into three portions: a proximal main portion 108, a distal end flared portion 110, and a tapered portion 112 positioned between main portion 108 and flared portion 110. The depicted embodiment is configured to be mounted at the end of a telerobotic instrument manipulator arm in a da Vinci® surgical system, commercialized by Intuitive Surgical, Inc., Sunnyvale, Calif. Cannula 100 is configured to receive and support telerobotically operated, minimally invasive surgical instruments with long shafts that have an outer diameter of about 5 mm. It should be understood that other cannulas that include aspects of the invention may be made to work with different surgical systems and with instruments having various outer diameters. And, various structural variations may exist. For example, a mounting section may be placed between the opposite ends of a tube section.

In one implementation, cannula 100 and its component sections 102, 104, and 106 are made of 316L stainless steel. Stainless steel is sterilizable (e.g., by autoclaving), which allows cannula 100 to be used many times. Stainless steel is electrically conductive, and so cannula 100 is subject to receiving and maintaining an electric charge via capacitive coupling, as described above. Persons of skill in the art will understand that surgical instruments, such as cannula 100, may be made of various materials that are capable of receiving an electric charge via capacitive coupling. In the depicted embodiment, cannula 100's overall length is about 6.061 inches.

The mounting section 102 includes two raised, annular mounting rings 114 that are configured to mate with a jawed cannula mounting bracket 116 (shown in partial schematic outline in FIG. 1B). The cannula mounting bracket jaws reach part way around the mounting section 102 in order to secure the cannula to the manipulator arm. But, since the mounting bracket jaws do not fully reach around mounting section 102, plug section 106 is positioned within the gap 118 left by the cannula mounting bracket jaws, as shown in the depicted embodiment. In other embodiments, however, plug section 106 may be placed at an alternate location on mounting section 102, or it may be coupled to tube section 104, so that an electrically conductive path may be established from the cannula to, e.g., a reference electrical potential that has been established for patient safety.

The proximal interior of mounting section 102 is tapered to help guide the distal end of a minimally invasive instrument into the cannula tube section 104 when the instrument is first inserted into the cannula. In the depicted embodiment, mounting section 102's proximal interior is "bowl-shaped", and various other shapes may be used to receive and guide an instrument into the cannula tube. The distal interior of mounting section 102 is a cylindrical bore that is shaped to receive the proximal end of tube section 104. In the depicted embodiment, tube section 104 is first press fitted into mounting section 102 and then laser welded in place. Various other fabrication methods may be used, to include forming mounting section 102 and tube section 104 out of a single piece, or subdividing mounting section 102 and tube section 104 into subcomponents.

As described above, the depicted embodiment shows that tube section 104 is divided into proximal main portion 108, an intermediate tapered portion 112, and distal end flared portion 110. For the depicted embodiment, the inner diameter of main portion 108 is substantially constant along its length and is about 0.380 inches. The inner diameter of tapered portion 112 slowly decreases proximally to distally, so that a minimum inner diameter for the tube section 104 occurs at or substantially at the distal end 120 of tapered portion 112. For the depicted embodiment, the taper is about 0.70 degrees each side, and the inner diameter at the distal end 120 is about 0.343 inches. Then, the inner diameter increases in the "trumpet"-shaped flared portion 110. For the depicted embodiment, the flare is based on a 0.235-inch radius. For ease of manufacturing, the tube section 104 wall thickness is kept relatively constant, so that the outer diameter of main portion 108 is substantially constant along its length, the outer diameter of tapered portion 112 tapers distally similarly to its inner diameter, and the outer diameter of flared portion increases. The outer diameter of the distal end lip 122 of flared portion 110 (i.e., the distal end of tube section 104) is finished to be full round at a radius of about 0.008 inches. The outer diameter of flared portion 110 is about 0.410 inches for the depicted embodiment.

The long, straight shaft of a minimally invasive surgical instrument that extends through the cannula is substantially rigid, but it has some resilient "bendiness" (i.e., it has sufficient stiffness to be effectively rigid for accurate telerobotic control, but minor flexing may occur during use, depending upon material properties and dimensions). Thus, for a situation in which the distal end of the instrument extends far enough beyond the distal end of the cannula, the distal end of the cannula acts as a fulcrum to the instrument shaft as a lever, and a portion of the instrument shaft inside the cannula is forced against the cannula side wall. And, since the cannula is long, the shaft typically bends ("bows") inside the cannula. This bending and forced contact between the instrument shaft and the interior cannula sidewall increases friction (static, dynamic, and stick-slip characteristics) so that in some instances it is difficult to achieve smooth servo-controlled instrument insertion and withdrawal through the cannula, and in other instances the instrument may become temporarily jammed inside the cannula until the distal side load on the instrument is reduced or eliminated. The tapered portion 112 allows the cannula's distal end inner diameter to be close enough to the instrument shaft's outer diameter to effectively guide the instrument shaft with the required precision, while the inner diameter of the main portion 108 is made larger to allow the instrument shaft to bend slightly inside the cannula. This tapering aspect is incorporated in existing cannulas used in da Vinci® surgical systems.

In accordance with an aspect of the invention, the flared portion 110 provides a smooth surface against which the instrument shaft slides during insertion and withdrawal. This smooth surface prevents scraping contact between the cannula's distal end and the instrument shaft. As mentioned above, for typical cannula insertion through a patient's body wall, an obturator is inserted through the cannula. As the obturator/cannula combination is inserted, the obturator tip pierces the body wall, which allows the cannula and obturator combination to be pushed through the body wall. But even a small distal end cannula flare, such as flared portion 110, makes it difficult to initially insert an obturator/cannula combination through a body wall. For use in telerobotic surgical procedures in which the cannula is not inserted through a body wall, such as transoral robotic surgery (TORS) in which one or more cannulas are positioned cantilevered within the patient's oral cavity, the need for body wall insertion is eliminated, and so a distal end flare may be used.

In accordance with another aspect of the invention, plug section 106 provides an electrical contact for cannula 100. Plug section 106 includes an electrically conductive housing 124 and two electrically conductive male prongs 126 that are press fit and then laser welded into housing 124. Housing 124 is then press fit and laser welded into a receptacle feature formed in mounting section 102. Thus, all portions of cannula 100 are in electrical contact with prongs 126, so that electric charge that builds up on cannula 100 may be drained via prongs 126 in plug section 106. In the depicted embodiment, plug section 106 is configured to receive an electrical connector (e.g., a female plug for the depicted embodiment) of a commercially available patient return electrode. Plug section 106 may be modified to electrically connect with various patient return electrode plug configurations.

Figure 2:
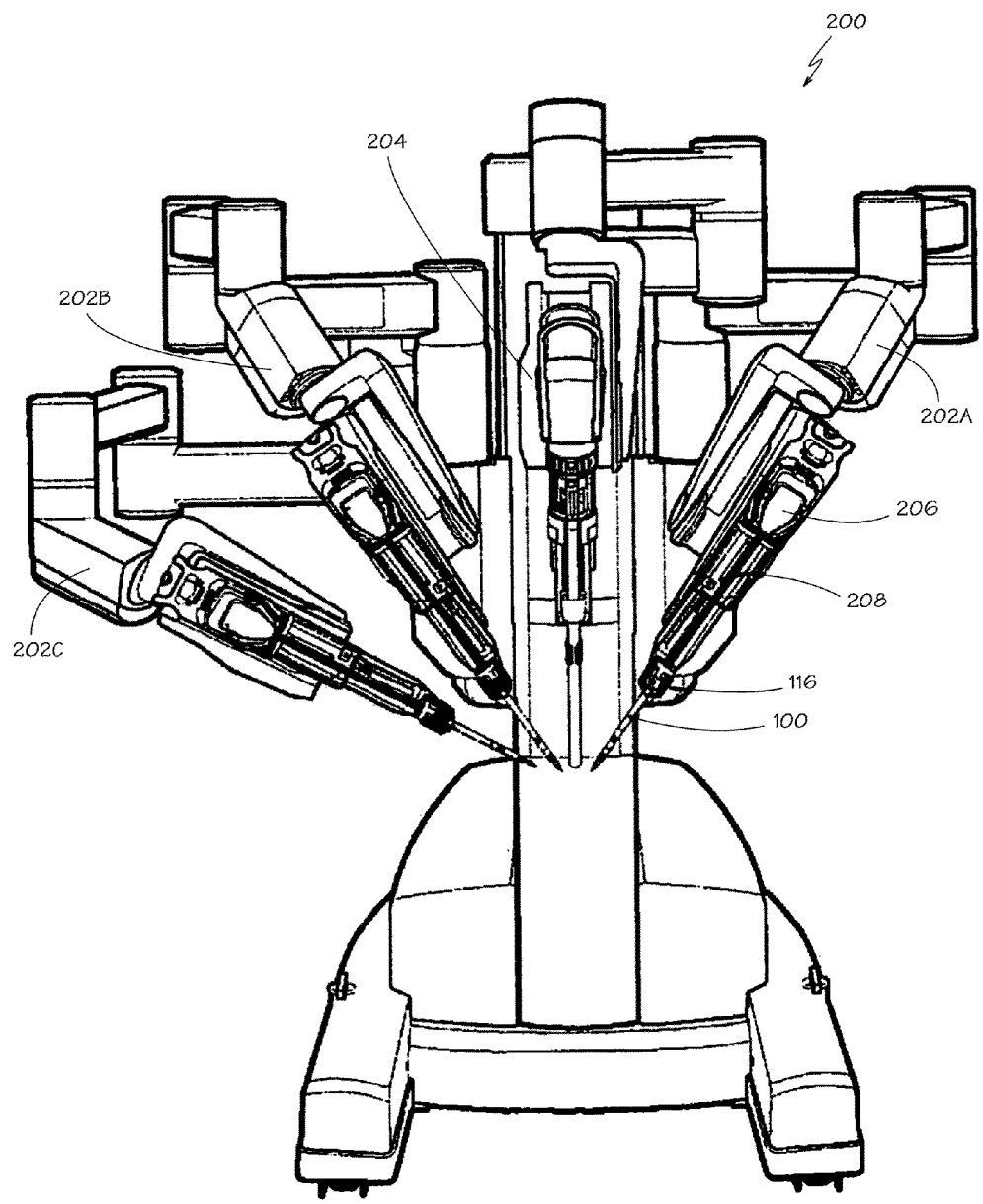
FIG. 2 is a front view of a patient-side unit of a telerobotic surgical system.

FIG. 2 is a front view of a patient-side (slave) unit 200 of a telerobotic surgical system. The associated surgeon's (master) unit and image processing/core computation unit are not shown. The depicted embodiment is a da Vinci® S (model no. IS2000) patient-side unit. Patient-side unit 200 includes three telerobotic instrument manipulators 202a-202c and a single telerobotic endoscopic camera manipulator 204. A cannula 100 is shown mounted at the end of instrument manipulator 202a to illustrate how cannula 100 is positioned with reference to other system components. One or more similar cannulas 100 may be mounted on manipulators 202b and/or 202c. A removable teleoperated minimally invasive surgical instrument surgical instrument 206 is illustratively shown mounted on instrument manipulator 202a so that instrument shaft 208 extends through cannula 100. Surgical instrument 206's distal end surgical end effector 210 extends beyond cannula 100's distal end. During surgery, one or more instrument manipulators are positioned to place the surgical instrument end effectors at a surgical work site. An endoscope 212 is mounted to endoscopic camera manipulator 204, which is positioned so that the surgical work site and the instrument end effectors are within endoscope 212's field of view. The surgeon controls the positions and orientations of the various surgical end effectors and the endoscopic camera by making teleoperation master control inputs at the surgeon's unit.

Figure 3:
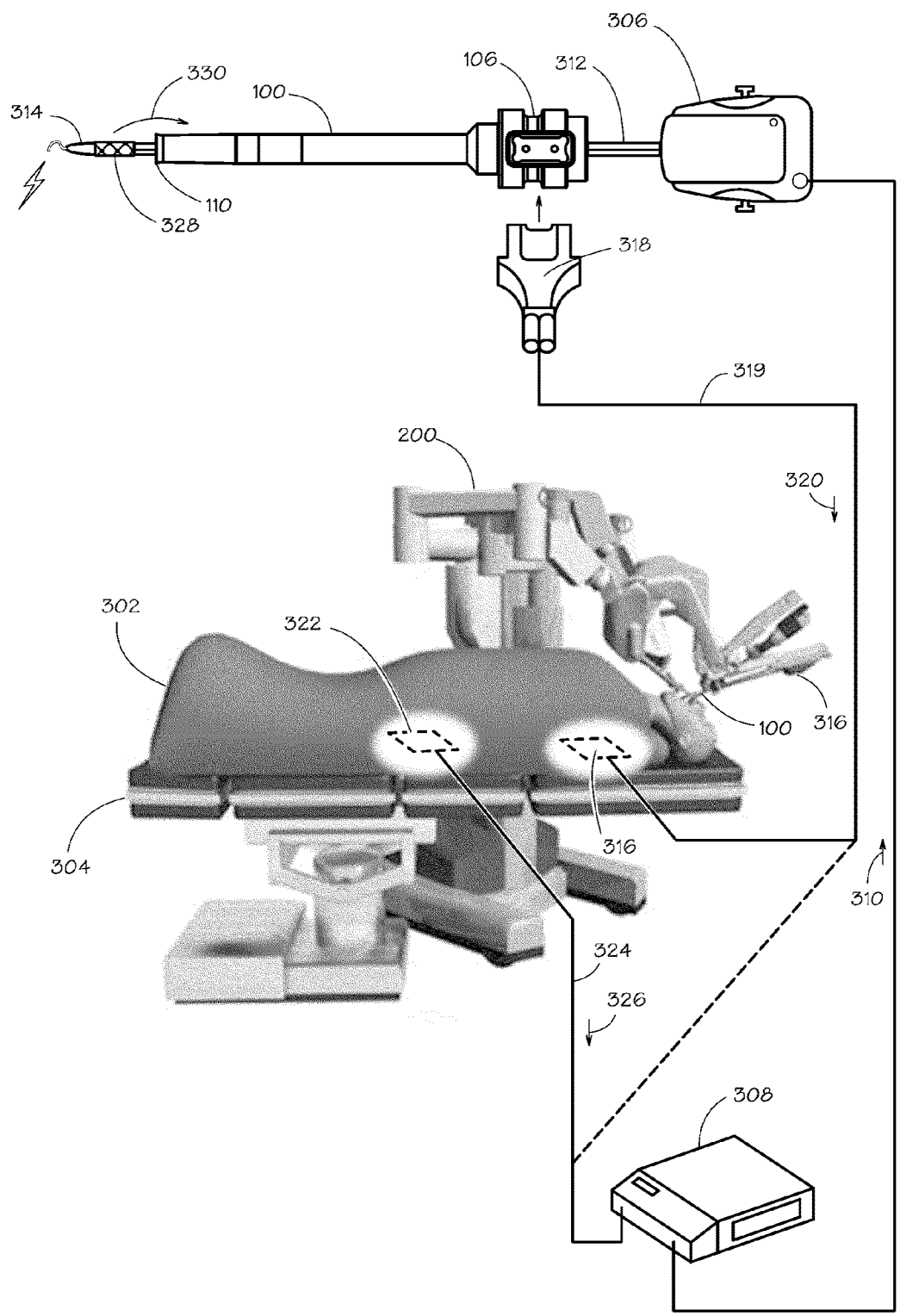
FIG. 3 is a diagrammatic view that illustrates an apparatus and method of removing electric charge from a cannula.

FIG. 3 is a diagrammatic view (not to scale) that illustrates further aspects of the invention. As depicted, a patient 302 is positioned on an operating room table 304 for an illustrative TORS procedure. Other surgical procedures in which a cannula does not contact the patient may be similarly carried out. Patient-side surgical unit 200 is placed so that its manipulator arms are positioned to introduce instruments through the patient's mouth and into the oral cavity. One such instrument 306 is an electrosurgical monopolar cautery hook instrument 306, which is inserted through cannula 100. Cannula 100 does not contact the patient. Instrument 306 is electrically coupled to electrosurgical generator unit 308, which supplies cautery energy 310 to instrument 306. The cauterizing energy passes through instrument shaft 312 (e.g., via an insulated electrically conductive cable) to reach cautery hook end effector 314. A first patient return electrode 316 is placed in contact with patient 302 (e.g., placed under the patient's shoulder area, as depicted). Return electrode 316 is electrically coupled via electrically conductive cable 319 to plug 318, which is inserted into cannula 100's plug section 106. The plug 318 and plug section 106 combination provides a quick, easy way to connect and disconnect the cannula to the discharge path, which is advantageous for use with relatively complex telerobotic manipulator arm positioning for certain surgical procedures. Thus, an electrical contact is made between patient 302 and cannula 100. Electric charge that may build up on cannula 100 is drained as current 320 to patient 302. This electrical connection prevents potentially injuring electric arcing between cannula 100 and patient 302.

FIG. 3 further depicts a second patient return electrode 322 placed in contact with patient 302 (e.g., under the patient's buttocks area, as depicted). This second return electrode is electrically coupled via cable 324 to electrosurgical energy generator unit 308 so that current 326 passes to unit 308. This current includes energy from end effector 314 from electrocautery use, as well as any charge from cannula 100. Consequently, there is an electrically conductive path that runs from cannula 100, through cable 319, through patient 302, and through cable 324 to generator unit 308. This path provides a safe electrical potential for cannula 100. In an alternative implementation, cannula 100 may be electrically coupled directly to generator unit 100, as depicted by the dashed line, or to a separate reference potential (not shown). Persons familiar with surgical procedures will understand that for safety the patient is typically not electrically coupled to an electrical earth ground, and so the reference electrical potential for the patient typically "floats" with reference to earth ground.

FIG. 3 also illustrates that an unwanted electric charge on a component of instrument 306 can be drained via capacitive coupling in accordance with an aspect of the invention. For example, even though instrument 306's flexible wrist mechanism 328 is electrically insulated from instrument 306's cautery energy components, an unwanted charge may nevertheless build up on wrist mechanism 328. But since instrument 306 extends through cannula 100, any unwanted charge on one or more of instrument 306 components may be transferred to cannula 100 via capacitive coupling between the instrument component(s) and the cannula, as indicated by arrow 330. Thus, even if a small gap or other insulation exists between the instrument component with the unwanted charge and the cannula, unwanted charge that would otherwise build up is conducted away from the instrument component first to the cannula and then away from the cannula as describe above. As a result of the capacitive coupling that exists between the instrument and the cannula, unwanted charge levels on one or more instrument component are minimized or removed, which prevents potential patient injury from arcing between the instrument component(s) and the patient.

The return electrodes 316,322 are depicted under the patient, although it should be understood that such electrodes may be placed in contact with the patient at various body locations.

We claim:

1. A cannula comprising:
   a plug section configured to receive an electrically conductive connector; and
   a tube section electrically coupled to at least a part of the plug section that contacts the electrically conductive connector;
   wherein the tube section is rigid and comprises a material capable of receiving an electric charge via capacitive coupling; and
   wherein the tube section comprises in series a proximal main portion, an intermediate tapered portion, and a distal end flared portion, the main portion having an inner diameter that is substantially constant, the tapered portion having an inner diameter that decreases from the inner diameter of at the main portion a proximal end of the tapered portion to a minimum inner diameter at a distal end of the tapered portion, and the flared portion having an inner diameter that increases from the minimum inner diameter of the tapered portion to a distal end of the tube section.

2. The cannula of claim 1, further comprising:
   a mounting section;
   wherein the tube section is coupled to the mounting section;
   wherein the mounting section allows a cannula mount to grasp and hold the mounting section with jaws that reach part way around the mounting section and leave a gap on the mounting section; and
   wherein the plug section is coupled to the mounting section in the gap on the mounting section.

3. The cannula of claim 2:
   wherein the plug section, the mounting section, and the tube section each comprise stainless steel.

4. The cannula of claim 1, wherein the tapered portion has a taper that is less than 1 degree on each side of the tapered portion.

5. The cannula of claim 1, wherein the minimum inner diameter of the tapered portion is about nine-tenths of the inner diameter of the main portion.

6. The cannula of claim 1, wherein a flare of the flared portion is based on a radius of about six-tenths of the inner diameter of the main portion.

7. An apparatus comprising:
   an electrosurgical energy generator unit;
   an electrosurgical instrument, wherein the electrosurgical instrument is coupled to receive electrosurgical energy from the generator unit;
   a cannula, wherein the cannula comprises an electrically conductive plug section and a tube section, wherein the tube section comprises a material capable of receiving an electric charge via capacitive coupling, and wherein the tube section is rigid and comprises in series a proximal main portion, an intermediate tapered portion, and a distal end flared portion, the main portion having an inner diameter that is substantially constant, the tapered portion having an inner diameter that decreases from the inner diameter of at the main portion a proximal end of the tapered portion to a minimum inner diameter at a distal end of the tapered portion, and the flared portion having an inner diameter that increases from the minimum inner diameter of the tapered portion to a distal end of the tube section; and an electrically conductive path between the plug section of the cannula and the generator unit, wherein the electrically conductive path comprises a plug configured to mate with at least a portion of the plug section of the cannula.

8. The apparatus of claim 7:
wherein the electrically conductive path further comprises a first cable that extends between the plug and a first patient electrode and a second cable that extends between a second patient electrode and the generator unit.

9. The apparatus of claim 7:
wherein the electrically conductive path further comprises a cable that extends directly between the plug and the generator unit.

10. The apparatus of claim 7, further comprising:
a telerobotic surgical system manipulator that includes cannula mounting bracket jaws;
wherein the cannula is removably mounted to the manipulator and held by the cannula mounting bracket jaws that reach part way around a mounting section of the cannula and leave a gap, the electrically conductive plug section of the cannula being positioned in the gap between the cannula mounting bracket jaws.

11. The apparatus of claim 7:
wherein the cannula is positioned sufficiently close to the electrosurgical instrument to receive, via capacitive coupling, an unwanted charge on a component of the electrosurgical instrument that occurs as a result of the electrosurgical energy.

12. An assembly comprising:
a cannula having a rigid tube section; and
a surgical instrument having a substantially rigid shaft;
the tube section comprising in series a proximal main portion, an intermediate tapered portion, a distal end flared portion, and a distal end;
the main portion having a constant inner diameter along a length of the main portion;
the tapered portion having an inner diameter that decreases from the inner diameter of the main portion at a proximal end of the tapered portion to a minimum inner diameter at a distal end of the tapered portion;
the flared portion having an inner diameter that increases along the length of the flared portion from the minimum inner diameter of the tapered portion to the distal end of the tube section; and
the shaft of the surgical instrument extending through the tube section, the shaft of the surgical instrument contacting the tube section only at the minimum inner diameter of the tapered portion.

13. The assembly of claim 12, the flared portion having an outer diameter that increases along the length of the flared portion to the distal end of the tube section.

14. The assembly of claim 12, the cannula further comprising:
a mounting section coupled to the tube section, the mounting section allowing a cannula mount to grasp and hold the mounting section.

15. The assembly of claim 14, further comprising:
an electrically conductive plug section;
the plug section being electrically coupled to at least a portion of the tube section;
the plug section being coupled to the mounting section.

16. A method comprising:
positioning a cannula to guide a shaft of a minimally invasive electrosurgical instrument into a patient without the cannula contacting the patient, wherein the cannula comprises an electrically conductive plug section and a tube section, wherein the tube section comprises a material capable of receiving an electric charge via capacitive coupling, and wherein the tube section is rigid and comprises in series a proximal main portion, an intermediate tapered portion, and a distal end flared portion, the main portion having an inner diameter that is substantially constant, the tapered portion having an inner diameter that decreases from the inner diameter of at the main portion a proximal end of the tapered portion to a minimum inner diameter at a distal end of the tapered portion, and the flared portion having an inner diameter that increases from the minimum inner diameter of the tapered portion to a distal end of the tube section;
inserting the shaft of the electrosurgical instrument through the cannula so that a distal end of the electrosurgical instrument extends into the patient;
coupling the electrosurgical instrument to receive electrosurgical energy from an electrosurgical generator unit; and
establishing an electrically conductive path between the cannula and the generator unit.

17. The method of claim 16:
wherein positioning the cannula comprises mounting the cannula to a telerobotic surgical system manipulator, holding the cannula with jaws that reach part way around the cannula and leave a gap around the coupling between the electrosurgical instrument and the electrosurgical generator unit, and positioning the manipulator to orient the shaft of the electrosurgical instrument for insertion into the patient.

18. The method of claim 16:
wherein establishing the electrically conductive path comprises connecting a first electrical connector to a corresponding second electrical connector on the cannula.

19. The method of claim 16:
wherein establishing the electrically conductive path further comprises establishing an electrically conductive path between the cannula and a first electrode in contact with the patient and establishing an electrically conductive path between the generator unit and a second electrode in contact with the patient.

20. The method of claim 19:
wherein establishing the electrically conductive path between the cannula and the first electrode comprises connecting a first electrical connector to a corresponding second electrical connector on the cannula.

21. The method of claim 16:
wherein establishing the electrically conductive path comprises establishing an electrically conductive path directly between the cannula and the generator unit.

22. The method of claim 21:
wherein establishing the electrically conductive path directly between the cannula and the generator unit comprises connecting a first electrical connector to a corresponding second electrical connector on the cannula.

23. The method of claim 16, further comprising:
inducing an unwanted charge on a component of the electrosurgical instrument as a result of the electrosurgical instrument receiving the electrosurgical energy; and
conducting the unwanted charge from the component of the electrosurgical instrument via capacitive coupling to the cannula.

* * * * *